United States Patent
Hart et al.

(10) Patent No.: US 10,493,239 B2
(45) Date of Patent: Dec. 3, 2019

(54) TORQUE-BASED CATHETER ARTICULATION

(71) Applicant: Auris Health, Inc., Redwood City, CA (US)

(72) Inventors: J. Scot Hart, Menlo Park, CA (US); Francis Macnamara, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 260 days.

(21) Appl. No.: 15/467,451

(22) Filed: Mar. 23, 2017

(65) Prior Publication Data

US 2017/0209672 A1    Jul. 27, 2017

Related U.S. Application Data

(63) Continuation of application No. 14/867,980, filed on Sep. 28, 2015, now Pat. No. 9,636,483, which is a
(Continued)

(51) Int. Cl.
*A61F 2/95*    (2013.01)
*A61F 11/00*   (2006.01)
(Continued)

(52) U.S. Cl.
CPC ......... *A61M 25/0147* (2013.01); *A61B 34/30* (2016.02); *A61B 34/37* (2016.02);
(Continued)

(58) Field of Classification Search
CPC .... A61F 2/95; A61F 2/04; A61F 2/958; A61F 11/00; A61B 34/00; A61B 34/37;
(Continued)

(56) References Cited

U.S. PATENT DOCUMENTS 2,556,601 A    6/1951 Schofield
2,566,183 A    8/1951 Forss
(Continued)

FOREIGN PATENT DOCUMENTS

CN    101500470    8/2009
CN    102665590    9/2012
(Continued)

OTHER PUBLICATIONS

European Search Report for patent application No. 14160090.8, dated Feb. 5, 2015.
(Continued)

*Primary Examiner* — Vi X Nguyen
(74) *Attorney, Agent, or Firm* — Knobbe, Martens, Olson & Bear, LLP

(57) ABSTRACT

A robotic surgical system configured for the articulation of a catheter includes an input device, a control computer, and an instrument driver having at least one motor for displacing the pull-wire of a steerable catheter wherein the control computer is configured to determine the desired motor torque or tension of the pull-wire of a catheter based on user manipulation of the input device. The control computer is configured to output the desired motor torque or tension of the pull-wire to the instrument driver, whereby at least one motor of the instrument driver implements the desired motor torque to cause the desired pull-wire tension to articulate the distal tip of the catheter.

13 Claims, 10 Drawing Sheets

Related U.S. Application Data continuation of application No. 13/828,342, filed on Mar. 14, 2013, now Pat. No. 9,173,713.

(51) Int. Cl.
| | |
|---|---|
| *A61M 25/01* | (2006.01) |
| *A61B 34/00* | (2016.01) |
| *A61B 34/30* | (2016.01) |
| *A61B 34/37* | (2016.01) |
| *A61B 90/00* | (2016.01) |

(52) U.S. Cl.
CPC .............. *A61B 34/71* (2016.02); *A61B 90/03* (2016.02); *A61B 2034/301* (2016.02); *A61B 2090/031* (2016.02); *A61B 2090/066* (2016.02); *A61M 2205/332* (2013.01); *A61M 2205/52* (2013.01)

(58) Field of Classification Search
CPC ............ A61B 34/71; A61B 2017/1205; A61B 2017/2929; A61B 2017/2825; A61M 25/01; A61M 25/0147
See application file for complete search history.

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,398,691 A | 3/1995 | Martin et al. |
| 5,408,409 A | 4/1995 | Glassman et al. |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,631,973 A | 5/1997 | Green |
| 5,713,946 A | 2/1998 | Ben-Haim |
| 5,749,362 A | 5/1998 | Funda et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,859,934 A | 1/1999 | Green |
| 5,876,325 A | 3/1999 | Mizuno et al. |
| 5,921,968 A | 7/1999 | Lampropoulos et al. |
| 5,951,475 A | 9/1999 | Gueziec et al. |
| 5,967,934 A | 10/1999 | Ishida et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,226,543 B1 | 5/2001 | Gilboa et al. |
| 6,259,806 B1 | 7/2001 | Green |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,155,315 B2 | 12/2006 | Niemeyer et al. |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,291,791 B2 | 10/2012 | Light et al. |
| 8,746,252 B2 | 6/2014 | McGrogan et al. |
| 8,827,948 B2 | 9/2014 | Romo et al. |
| 8,894,610 B2 | 11/2014 | MacNamara et al. |
| 8,961,533 B2 | 2/2015 | Stahler et al. |
| 9,138,166 B2 | 9/2015 | Wong et al. |
| 9,173,713 B2 | 11/2015 | Hart et al. |
| 9,204,933 B2 | 12/2015 | Reis et al. |
| 9,254,123 B2 | 2/2016 | Alvarez et al. |
| 9,326,822 B2 | 5/2016 | Lewis et al. |
| 9,408,669 B2 | 8/2016 | Kokish et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0117017 A1 | 8/2002 | Bernhardt et al. |
| 2002/0161355 A1 | 10/2002 | Wollschlager |
| 2002/0177789 A1 | 11/2002 | Ferry et al. |
| 2004/0015053 A1 | 1/2004 | Bieger |
| 2004/0152972 A1 | 8/2004 | Hunter |
| 2004/0243147 A1 | 12/2004 | Lipow |
| 2005/0183532 A1 | 8/2005 | Najaf et al. |
| 2005/0222554 A1 | 10/2005 | Wallace et al. |
| 2006/0025676 A1 | 2/2006 | Viswanathan et al. |

(56) References Cited

U.S. PATENT DOCUMENTS

| | | |
|---|---|---|
| 2006/0111692 A1 | 5/2006 | Hlavka et al. |
| 2006/0201688 A1 | 9/2006 | Jenner et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0112355 A1 | 5/2007 | Salahieh |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1* | 2/2008 | Manzo ............. A61B 1/00149 700/245 |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0247944 A1 | 10/2009 | Kirschenman et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130987 A1 | 5/2010 | Wenderow et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0280320 A1 | 11/2010 | Alvarez et al. |
| 2010/0280525 A1 | 11/2010 | Alvarez et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0123441 A1 | 5/2012 | Au |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0239012 A1 | 9/2012 | Laurent et al. |
| 2012/0283747 A1 | 11/2012 | Popovic |
| 2013/0018400 A1 | 1/2013 | Milton et al. |
| 2013/0030363 A1 | 1/2013 | Wong et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0222019 A1 | 8/2014 | Brudnick |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0001038 A1 | 1/2016 | Romo et al. |
| 2016/0007881 A1 | 1/2016 | Wong et al. |
| 2016/0151122 A1 | 6/2016 | Alvarez et al. |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0055589 A1 | 3/2018 | Joseph et al. |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 3 025 630 | 6/2016 |
| JP | 2009-139187 | 6/2009 |
| JP | 2010-046384 | 3/2010 |
| WO | WO 02/074178 | 9/2002 |

(56) References Cited

FOREIGN PATENT DOCUMENTS

| WO | WO 03/086190 | 10/2003 |
| WO | WO 03086190 A1 | 10/2003 |
| WO | WO 09/092059 | 7/2009 |
| WO | WO 11/005335 | 1/2011 |
| WO | WO 13/179600 | 12/2013 |
| WO | WO 15/127231 | 8/2015 |

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

Search Report for European Patent Application No. 14160090.8, dated Feb. 5, 2015 (6 pages).

\* cited by examiner

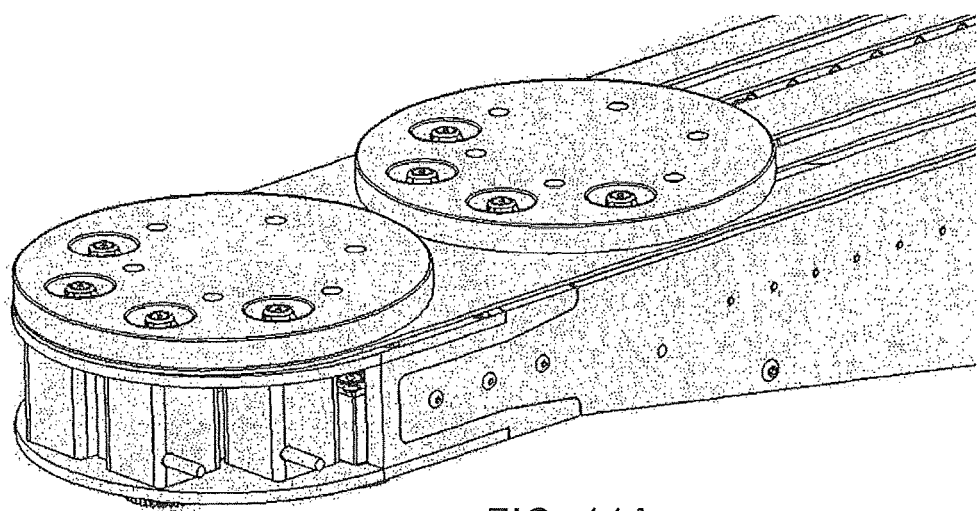
FIG. 11A
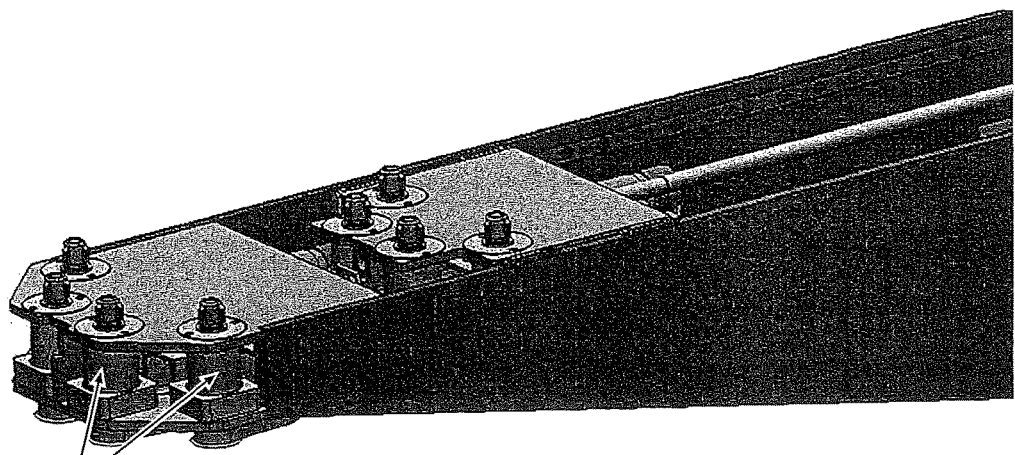
601  FIG. 11B

TORQUE-BASED CATHETER ARTICULATION

CROSS-REFERENCE TO RELATED APPLICATIONS

This application is a continuation of U.S. patent application Ser. No. 14/867,980, entitled "TORQUE-BASED CATHETER ARTICULATION," filed on Sep. 28, 2015, and published as U.S. Patent Application Publication No. 2016/0015937, which is a continuation of U.S. patent application Ser. No. 13/828,342, entitled "TORQUE-BASED CATHETER ARTICULATION," filed on Mar. 14, 2013, and issued on Nov. 3, 2015 as U.S. Pat. No. 9,173,713. The disclosure of the above-referenced patent applications is hereby incorporated by reference in their entirety herein.

FIELD OF THE PRESENT DISCLOSURE

The present disclosure generally relates to robotic surgical systems for performing minimally invasive diagnostic therapeutic procedures and particularly to robotic catheter systems for steerable catheters.

BACKGROUND

Robotic surgical systems and devices are well suited for use in performing minimally invasive medical procedures, as opposed to conventional techniques that may require large incisions to open the patient's body cavity to provide the surgeon with access to internal organs. For example, a robotic surgical system to be utilized to facilitate imaging, diagnosis, and treatment of tissues which may lie deep within a patient, and which may be preferably accessed only via naturally-occurring pathways such as blood vessels or the gastrointestinal tract.

One such robotic surgical system that may be utilized in a minimally invasive procedure is a robotic catheter system. A robotic catheter system utilizes a robot, external to the patient's body cavity, to insert a catheter through a small incision in a patient's body cavity and guide the catheter to a location of interest. Catheters may be steerable for movement in multiple axes including axial insertion/retraction, axial rotation, and deflection/articulation, which encompasses radial bending in multiple directions. To accomplish steering, one or more pull-wires are attached to the distal end of an articulating section of a catheter and extend the length of the catheter. The distal tip of a catheter may then be controlled via the pull-wires, i.e., by selectively operating tensioning control elements within the catheter instrument.

Kinematic modeling is utilized to predict catheter tip movement within the patient anatomy. The amount of displacement of a pull-wire is generally proportional to the amount of articulation. At times, the calculated motion of the catheter does not precisely match the actual motion within the patient's anatomy. Various elements can affect the amount of articulation for a given pull-wire actuation, including the presence of unanticipated or un-modeled constraints imposed by the patient's anatomy, particularly given the tortuous path that the catheter must traverse. Minimization of differences between actual and predicted kinematic functions is desirable to achieve a highly controllable robotic surgical system.

SUMMARY

A robotic surgical system may include at least one input device configured to output desired catheter positioning information; a control system operatively connected to the input device and configured to receive the positioning information from the input device and to translate the positioning information into at least one output motor torque command; at least one instrument driver operatively connected to the control system and responsive to the output motor torque command to articulate the distal portion of a catheter instrument, The control system of the robotic surgical system may include an algorithm in which at least one set of instructions defines a catheter movement profile using motor torque as an output to the instrument driver. The instrument driver of the robotic surgical system may also include at least one torque measuring device. The robotic surgical system may use closed loop feedback to sense any difference between actual motor torque and the output motor torque so as to adapt the electrical current to correct for any difference with the output motor torque and/or adapt kinematic parameters to determine adjustments to the output motor torque. A motor servo may use torque data from the torque measuring device to adjust the electrical current supplied to a motor. The control system may also use the torque data to adjust the operation parameters.

A method of articulating a catheter instrument in a robotic surgical device, comprising the steps of inserting a catheter instrument into an anatomical lumen of a patient; manipulating an input device to generate positioning information for a desired position for a distal portion of the catheter instrument which is steerable; communicated to a control system; converting the positioning information from the input device into at least one output motor torque; and communicating the output motor torque to an instrument driver thereby causing the instrument drive to articulate the distal end portion of the catheter instrument. The method may further include the step of measuring current motor torque. The method may further include the step of adjusting the electrical current of at least one motor in response to an error signal that current motor torque is different from the output motor torque.

BRIEF DESCRIPTION OF THE DRAWINGS

FIGS. 11A and 11B illustrate an exemplary torque sensor.

DETAILED DESCRIPTION

Figure 1:
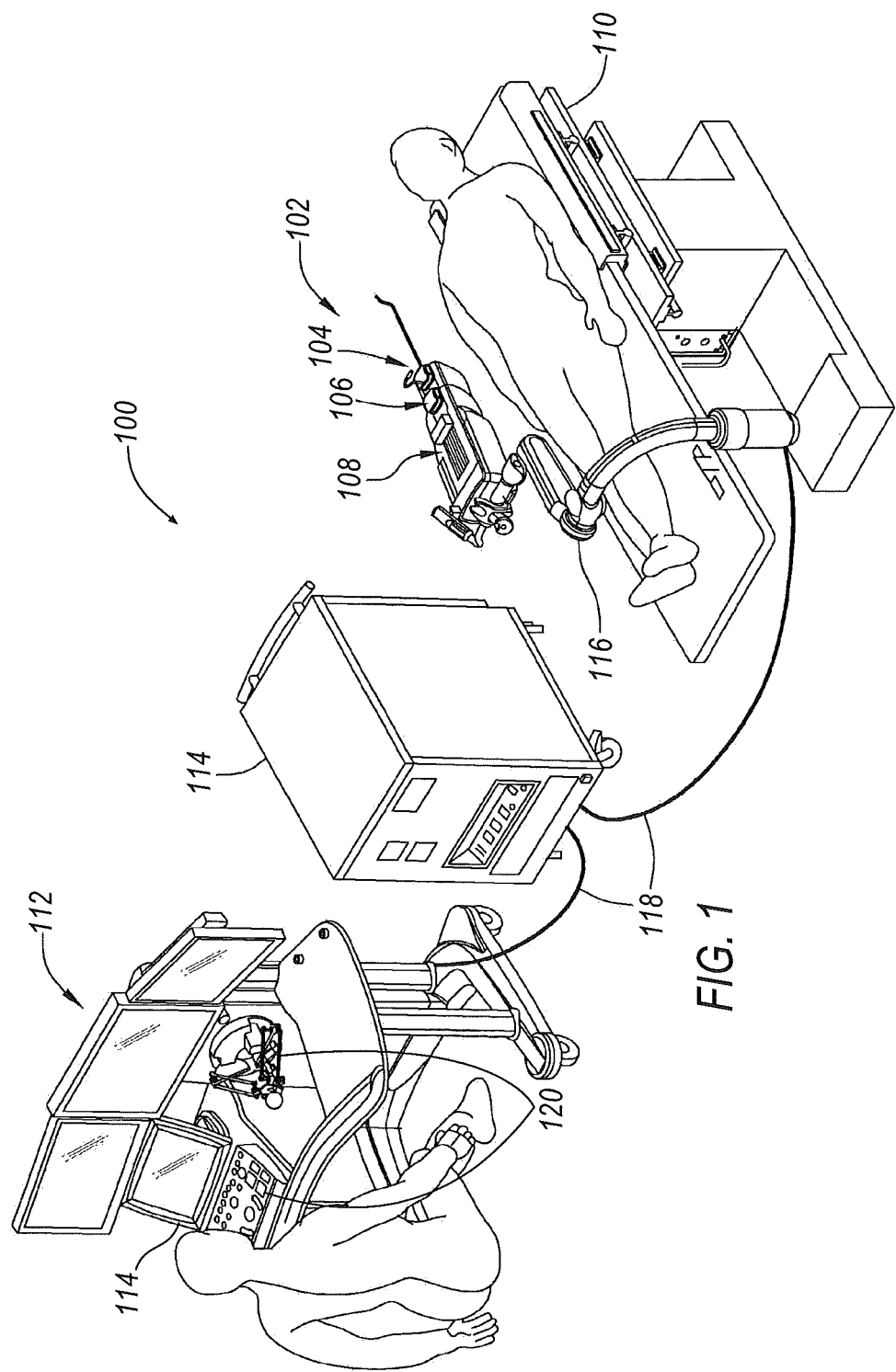
FIG. 1 illustrates an exemplary robotic surgical system.

Referring now to the discussion that follows and also to the drawings, illustrative approaches to the disclosed assemblies are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Referring to FIG. 1, a robotic surgical system 100 is illustrated in which an apparatus, a system, and/or method may be implemented according to various exemplary illustrations. System 100 may include a robotic catheter assembly 102 having a sheath instrument 104 and/or a catheter instrument 106. Catheter assembly 102 is controllable using a robotic instrument driver 108 (generally referred to as "instrument driver"). During use, a patient is positioned on an operating table or surgical bed 110 to which robotic instrument driver 108 is coupled or mounted. In the illustrated example, system 100 includes an operator workstation 112, an electronics rack 114 including a control computer (not shown), a setup joint mounting brace 116, and instrument driver 108. A surgeon is seated at operator workstation 112 and can monitor the surgical procedure, patient vitals, and control one or more catheter devices.

Operator workstation 112 may include a computer monitor to display a three dimensional object, such as a catheter displayed within or relative to a three dimensional space, such as a body cavity or organ, e.g., a chamber of a patient's heart. In one example, an operator uses one or more input devices 120 to control the position of a catheter or other elongate instrument. In response to actuation of the input device by a user, the input device can output positioning information for the desired position of the catheter instrument, including the three-dimensional spatial position of the distal end of a steerable catheter. System components, including the operator workstation, electronics rack and the instrument driver, may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while located away from or remotely from radiation sources. Because of the option for wireless or networked operation, the surgeon may even be located remotely from the patient in a different room or building.

Figure 2:
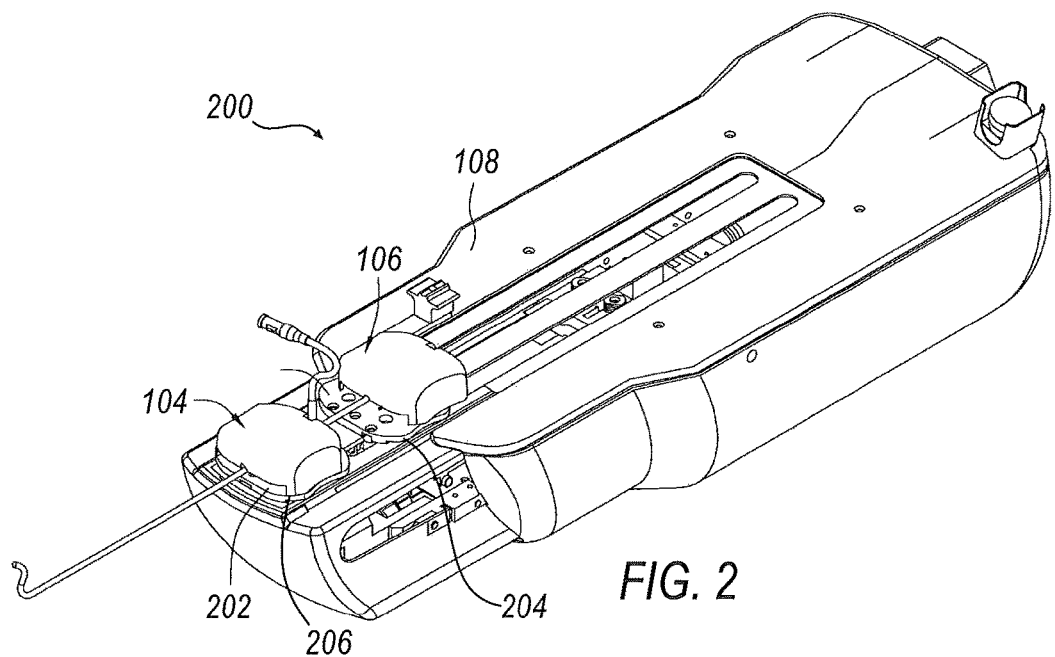
FIG. 2 is an illustration of an exemplary catheter assembly of the surgical system of FIG. 1.

Referring now to FIG. 2, motors within instrument driver 108 are controlled such that carriages coupled to mounting plates 204, 206 are driven forwards and backwards on bearings. As a result, a catheter can be controllably manipulated while inserted into the patient. Instrument driver 108 contains motors that may be activated to control bending of the catheter as well as the orientation of the distal tips thereof, including tools mounted at the distal tip.

Figure 3:
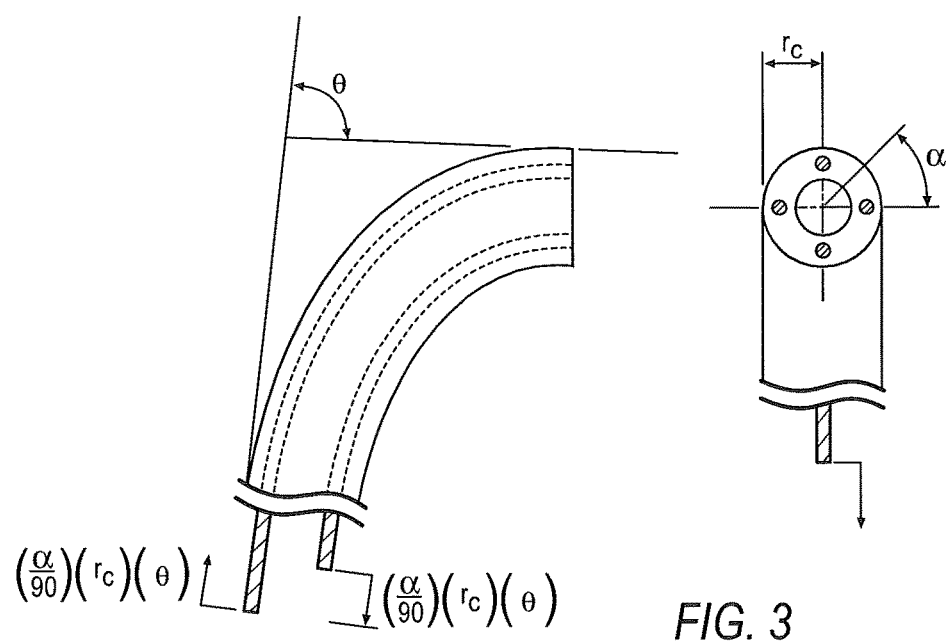
FIG. 3 is a schematic showing a kinematic relationship between pull-wire displacement and catheter tip articulation.

The articulation of catheters is normally performed by actuating pull-wires that extend the length of the catheter and are attached to the distal end of an articulating section of a catheter. In order to articulate the catheter, the pull-wire is displaced at the proximal end to articulate the distal end of the catheter. Typically, the amount that an articulating section of a catheter articulates is determined by calculating the change in path length that an actuating pull-wire takes. For a straight catheter, that length is equal to the articulating section, $L_o$. As the catheter bends (where $\alpha$ is the angle from the neutral axis, $r_c$ is the radius of the catheter, and $\tau$ is the articulation angle), the path length is equal to $L_o - \cos(\tau/90) *r_c*\tau$. The difference—$(\alpha/90)*r_c*\tau$—is the distance the pull-wire must be actuated to make a catheter articulate to an angle $\tau$, as illustrated in FIG. 3. From this concept, further solid mechanic and kinematic modeling is used via algorithms in the control computer to convert a desired catheter position or orientation as provided by the user into commands to the instrument driver to rotate motors designated for each pull-wire.

Figure 4:
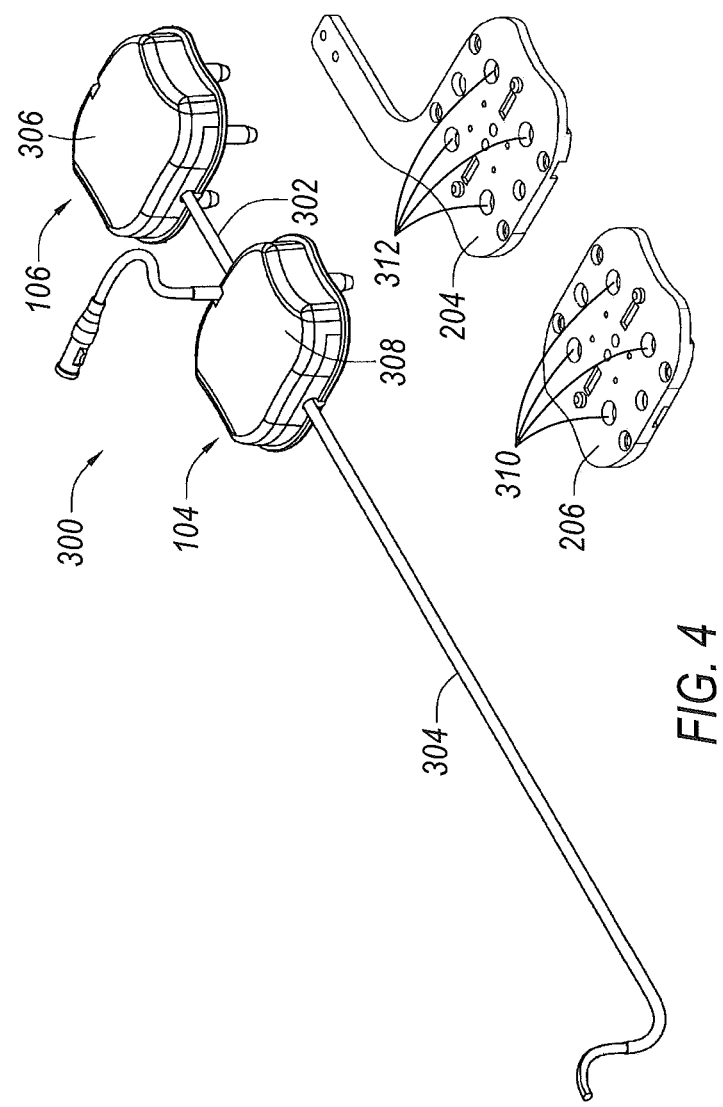
FIGS. 4 and 5 are partially exploded views of the catheter assembly of FIG. 2.
Figure 5:
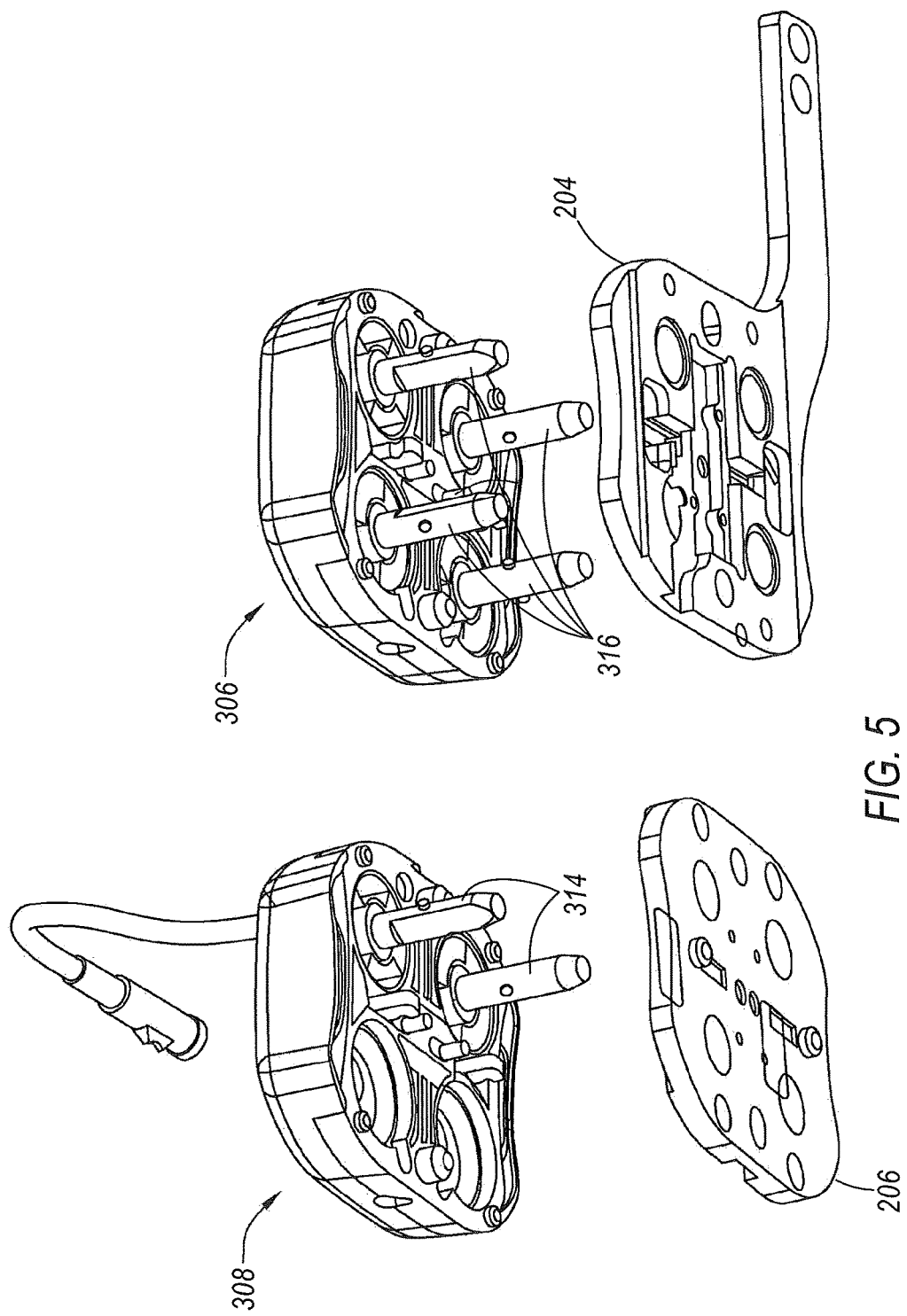

When a catheter is prepared for use with an instrument, its splayer is mounted onto its appropriate interface plate. In this case, as shown in FIG. 4, sheath splayer 308 is placed onto sheath interface plate 206 and a guide splayer 306 is placed onto guide interface plate 204. In the illustrated example, each interface plate 204, 206 has respectively four openings 310, 312 that are designed to receive corresponding drive shafts 314, 316 (FIG. 5 illustrates an underside perspective view of shafts 314, 316) attached to and extending from the pulley assemblies of the splayers 308, 306). Drive shafts 314, 316 are each coupled to a respective motor within instrument driver 108.

Figure 6:
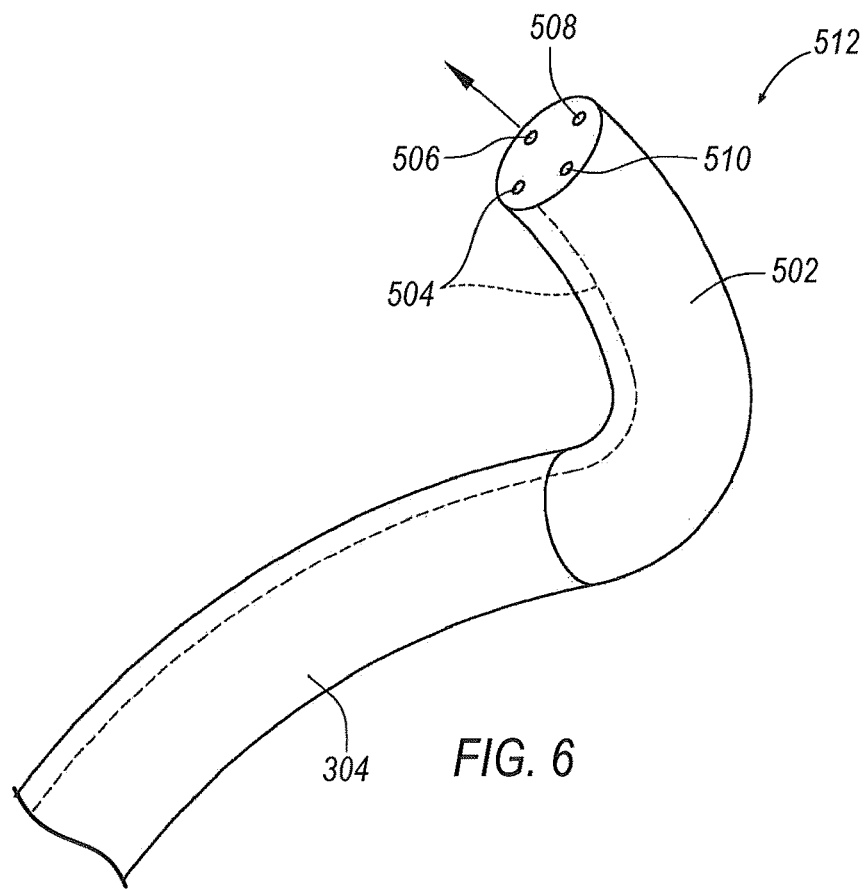
FIG. 6 illustrates an exemplary steerable catheter with pull-wires.

Embodiments with less or more than four pull-wires are contemplated by the present disclosure. When, e.g., a four-wire catheter 304 is coupled to instrument driver 108, each drive shaft 316 thereof is thereby coupled to a respective wire 504-510 (see FIG. 6). As such, a distal end 512 of catheter 304 can be articulated and steered by selectively tightening and loosening pull-wires 504-510. Typically, the amount of loosening and tightening is slight, relative to the overall length of catheter 304. That is, each wire 504-510 typically need not be tightened or loosened more than perhaps a few centimeters. As such, the motors that tighten/loosen each wire typically do not rotate more than, for example, ¾ of a rotation. Thus, given the solid mechanics and kinematics of directing the instrument driver, a catheter (or other shapeable instrument) may be controlled in an open-loop manner, in which the shape configuration command comes in to the beam mechanics and is translated to beam moments and forces, then translated into pull-wire tensions as an intermediate value before finally translated into pull-wire displacement given the entire deformed geometry. Based on the pull-wire displacement command, a motor servo can apply the appropriate electrical current to produce the amount of rotation required to displace the pull-wire.

Robotic systems use algorithms to determine the displacement of the pull-wires to achieve the desired articulation of a catheter. However, differences between predicted and actual catheter position can result from the reliance by the kinematic model on certain assumptions and the lack of certain information. With rigid kinematics, simple geometry can be used to predict the location of any point along the rigid object given the following information: (1) a reference coordinate system; (2) an origin, or point in any coordinate system attached to the object; and (3) an orientation in any coordinate system attached to the object. Even with rigid structures, external forces, even gravity, may disrupt the ability to solve the location equation given the information above. If the above information is not sufficient to accurately describe the position of one point of an object from another point on the same object, then additional information must be provided, like the weight of the object, the forces acting on the object, the strength of the object, etc.

Standard equations and constants, like Poisons ratio, Hertzian stresses, Modulus of Elasticity, and linear stress/strain equations can improve on the kinematic model but these methods break down once the strains exceed the standard elastic range (usually about 3%). For example, a slim bar may be straight under no distal loading and the equations to predict the location of the distal end are fairly effective. However, when a load is placed on the beam, the distal end will deflect, or strain under the load. Even in a purely elastic response to the load, the location or orientation of the distal end of the beam is impossible to predict without knowing the magnitude, the direction, and the location of the external load. Similarly, flexible instruments such as catheters with low strength can be deflected by unknown loads at unknown locations and in unknown directions. Yet, prediction of the location and orientation of the distal end of a catheter is an important aspect of a robotic catheter system. The orientation of the distal end of the catheter based on information measured at the proximal end can better be determined through embodiments of the present disclosure.

To enhance the transfer function between inputs and outputs, an embodiment of the present disclosure determines the output motor torque(s) corresponding to the desired tension in the pull-wires and the instrument driver 108 acts on the output motor torque command to articulate the catheter. A kinematic model for catheter articulation can translate positional data from the input device 120 at the workstation 112 into pull-wire displacement commands whereby the motor(s) of the instrument driver 108 are rotated in accord with that amount of displacement. In contrast, in an exemplary embodiment of the present disclosure, the positional data from input device 120 is translated into pull-wire tension values tied to motor torque, whereby the motors are rotated in accord with the value of the motor torque.

From a user standpoint, the system behaves much the same way in that the user provides desired catheter motions and the catheter follows. The difference is that by using desired pull-wire tension instead of desired pull-wire displacement, a number of advantages can be achieved. One advantage is the reduction in the number of assumptions in the kinematic model to increase accuracy. For example, with pull-wire displacement calculations, various non-rigid elements affect the amount of articulation for a given pull-wire actuation, including (1) pull-wire stiffness; (2) axial catheter stiffness and (3) actual catheter geometry, including the resultant stiffness of the bending or twisted section. The displacement of the pull-wire at the actuated or proximal end of the catheter is thus not equal to the displacement at the tip of the catheter, but rather a function of the various spring rates. For instance, a small pull-wire will stretch more per unit force and transmit less displacement to the distal tip than a stiffer one though both will transmit the same force.

Catheter movement may be predicted by modeling the catheter assembly as a system of springs. For example, if the following parameters are known:

$K_S$: Spring rate of catheter shaft (lbs/in)
$K_T$: Torsional Spring rate of bending section (in*lbs/radian)
$K_W$: Spring rate of pull-wires (lbs/in)

Figure 7:
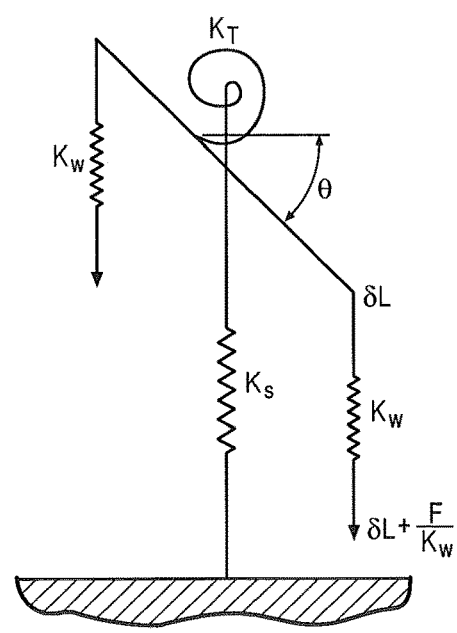
FIG. 7 is a model of a catheter assembly as a system of springs.

Further, $K_T$ is directly proportional to the Bending Stiffness (lb*in$^2$), where $K_T*L=K_B$ where L=Length of bending section. Then the entire catheter can be modeled as a spring system, as shown in FIG. 7. The use of pull-wire tension as the output parameter eliminates the need to make such assumptions. That is, the displacement at the tip can be calculated by solving the force equations instead of solving the displacement equation. The transfer function from input to output can thus be improved by commanding the instrument driver 108 with torque commands correlated to the desired output tensions for the one or more pull-wires in the catheter.

Figure 8:
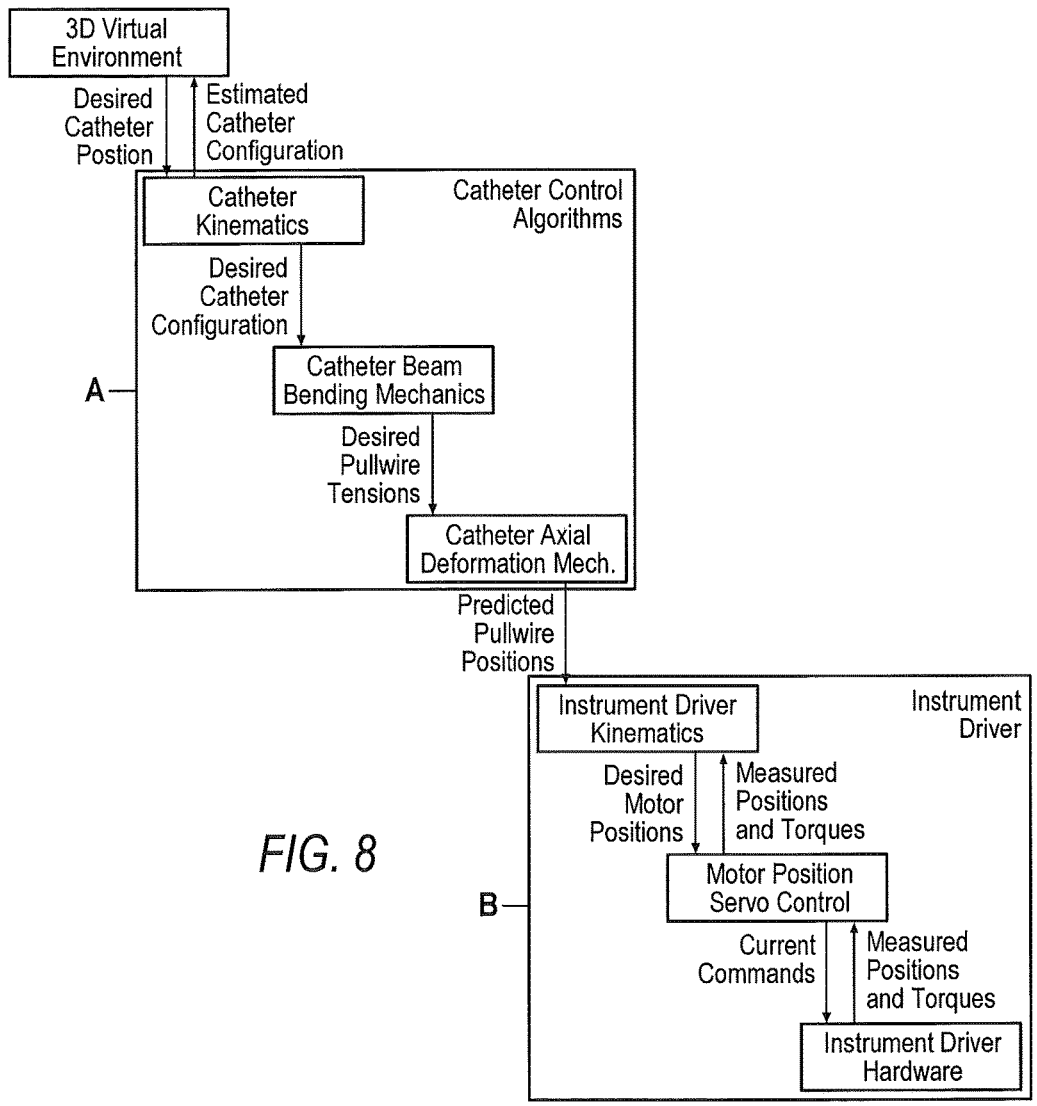
FIG. 8 is a flow diagram for catheter steering using desired motor position as an output to motor position servo control of the instrument driver.
Figure 9:
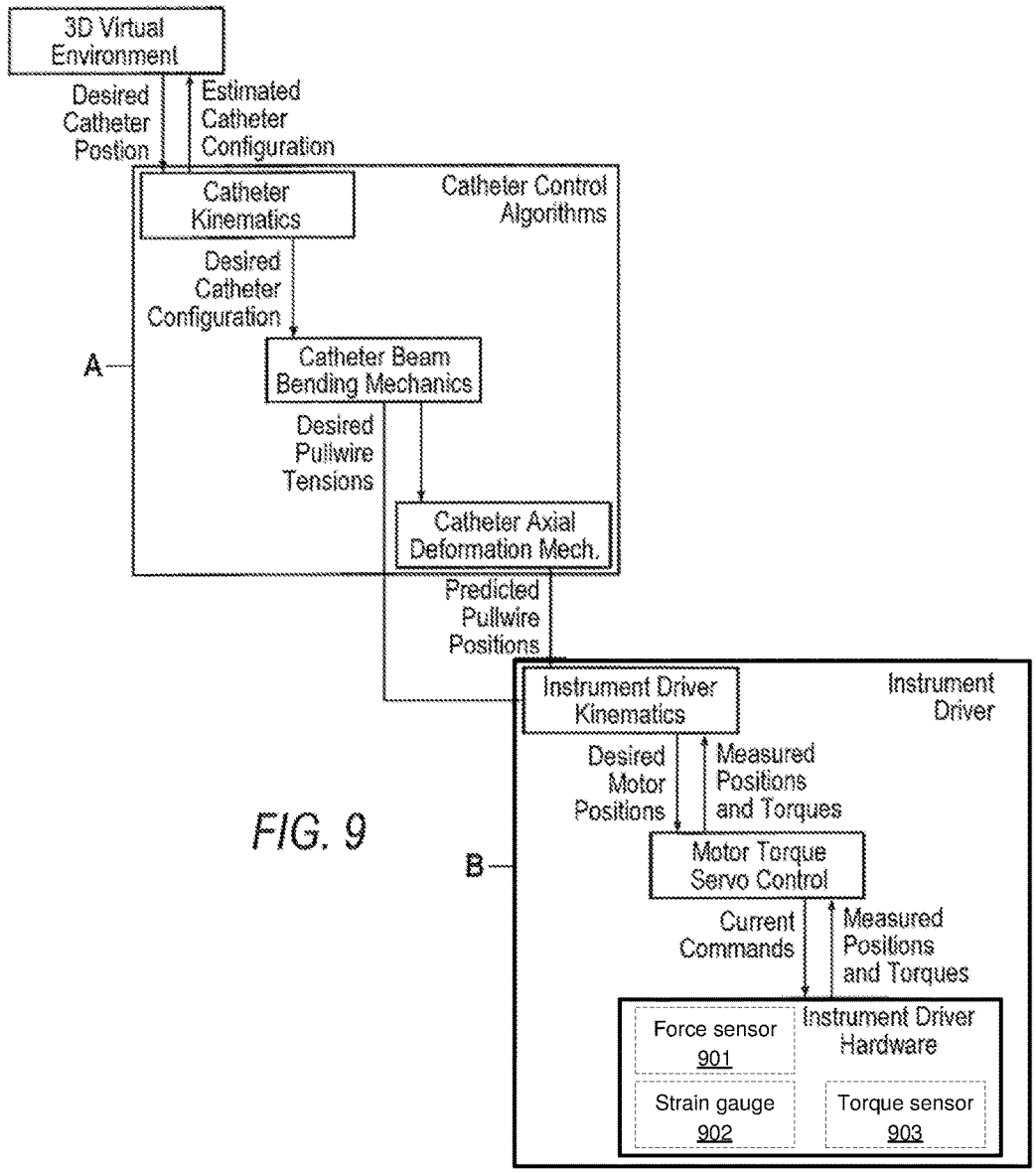
FIG. 9 is a flow diagram for catheter steering using desired motor torque as the output to the instrument driver.

Further, in an exemplary variation of that embodiment of the present disclosure, the high-level catheter control algorithm can be combined with a lower level motor torque control algorithm to accurately drive a catheter in response to a user's commands. Control algorithms may be split into several parts. One aspect of catheter control, as shown in FIGS. 8 and 9 in block A, may be a high-level open-loop algorithm combining catheter solid mechanics and kinematics to convert a desired catheter position or orientation as provided by the user into motor commands. Another aspect of catheter control, shown in FIGS. 8 and 9 in block B, may be a lower-level closed-loop motor servo controller that takes the motor commands produced by the catheter control algorithms and converts them to the motor current needed at every time step to achieve the desired catheter motion. FIG. 9 is an exemplary embodiment of the present disclosure illustrating the flow diagram for catheter steering using desired motor torque as the output to the instrument driver. Though a surgical system may control the catheter through the use of motor commands to the motor servos in the form of position commands, increased driving performance can be achieved by altering the architecture such that the motor command transferred to the motor servo controller is a desired motor torque.

Desired motor torques can be determined based on catheter solid mechanics and kinematics control algorithms. For example, the value of the desired tension of the catheter pull-wires can be used to determine the desired motor position. The desired pull-wire tension can be translated to a desired motor torque by multiplying the pull-wire tension by the radius of the pulleys in the splayers.

$$MotorTorque_{Desired}=PullWireTension_{Desired}*PulleyRadius$$

Once the desired motor torque is determined, the instrument driver 108 can apply the desired torques to the motors which in turn applies the desired tension to the pull-wires.

A model-based force control algorithm is an exemplary variation of an embodiment, having the advantages of extreme robustness and stable interaction with the possible passive environments seen at the output shaft of the motor. In the case of the articulation axes, each articulation motor may be treated as a single degree of freedom torque source, in which case for this embodiment, the model-based force control algorithm collapses into an integral controller on force error combined with direct feed-forward of the desired force and a viscous damping term.

Figure 10:
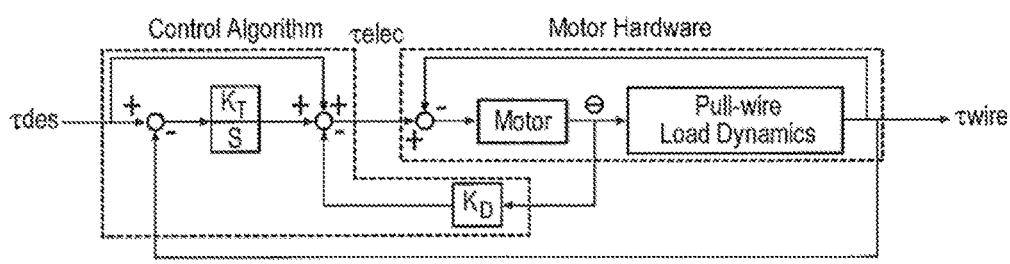
FIG. 10 is a model-based force control block diagram, which is one implementation of the embodiment shown in the flow diagram of FIG. 9.

FIG. 10 is a control block diagram modeling aspects of the flow diagram of FIG. 9 using model-based force control. Since the motor velocity and output torque are a function of both motor dynamics as well as the load produced by the pull-wire, the motor is not modeled as a simple transfer function given the inherently non-linear and time dependent pull-wire dynamics that are constantly changing depending on what the catheter is touching, what shape the catheter has, and how the catheter is being driven. Instead, the combined motor/catheter pull-wire system is modeled as a motor block which takes as an input the net torques applied to the motor ($\tau_{elec}-\tau_{wire}$) where $\tau_{elec}$ is the electrical torque provided by the amplifiers and calculated by the control algorithm and $\tau_{wire}$ is the reaction torque provided by the pull-wire. These torques combine with the motor dynamics to produce a motor velocity dO/dt which is then fed into the pull-wire dynamics to produce the torque applied to the pull-wire.

The benefits of the model-based force control algorithm arise in part from its stability for any passive pull-wire load dynamics regardless of non-linearity or complicated geometry. In this variation of one embodiment of the present disclosure, the model-based control algorithm does not allow the force controller to attempt to reject any of the motor's inertial forces as a disturbance in order to achieve a high level of stability. That is, the force control algorithm does not attempt to make the motor feel like it has less mass than it actually has. For this algorithm, the ratio $K_D/K_I$ must be greater than the inertia of the motor. Once implemented, the model-based control algorithm essentially works by rejecting any friction in the motor (or gearing) such that the resulting closed-loop system feels like an ideal frictionless motor with inertia $K_D/K_I$. At steady-state and with no acceleration, the integral term in the controller ensures complete friction rejection such that $\tau_{wire}=\tau des$. At all other times, the difference between $\tau_{wire}$ and $\tau$des is mostly the inertial force of the motor.

$$\tau_{des}-\tau_{wire} \approx J\alpha \text{ where } \alpha \text{ is the motor acceleration.}$$

The above approximation becomes more exact as control terms $K_D$ and $K_I$ become larger. Nevertheless, like any control algorithm, limitations exist on the size of the control gains without exciting other unmodeled dynamics in the system and driving the system to instability. The model-based force control strategy provides increased performance while still meeting robustness requirements and without reducing safety.

The model-based force control strategy is one exemplary implementation of the present disclosure. The torque-based strategy of the pull-wire tension control paradigm can be implemented with numerous possible force control algorithms could be used to get the motors to behave as desired. Further, multiple modifications can be added to the catheter control kinematics and solid mechanics to fine tune catheter driving performance. Exemplary modifications to the motor torque control servo algorithm include: (1) using additional control strategies to modify $\tau_{des}$ before sending to the motor servo controller; such as, adding additional damping for enhanced stability or simply for achieving more desirable dynamics; and (2) replacing the integral controller with a high gain, low pass filter to avoid problems (such as integral drift) that typically arise when using integral controllers.

In order to sense the tension in the catheter control wires, a torque measuring device can be utilized. One exemplary embodiment of the present disclosure, shown in FIGS. 5, 9, 11A and 11B, incorporates torque sensors 903 installed on the drive shafts 314, 316 that transmit motion from the motors to the pull-wires. A torque sensor 903 could be alternatively located in other areas of the system. An alternative method to measure torque may include a direct measurement of force on the pull-wires using a force sensor 901. An exemplary variation of that alternative method may involve using the pull-wire as a strain gauge 902.

In one embodiment, the tension in the pull-wire can be calculated simply by dividing the torque by the effective radius (rdrum+r wire) of the catheter control wire. Any difference between the actual and commanded motor torque value (an "error signal") can be used to make electrical current adjustments by a motor servo or the control computer to reduce or eliminate the error. Thus, knowledge of the tension (or force) being applied to the pull-wires permits close loop controlled of the catheter movement. Further, with the tension information available, control algorithms can improve the performance and control of the catheter. In some instances, the tension information can provide information about forces being applied to the catheter and can be fed back to the user haptically.

Figure 12A:
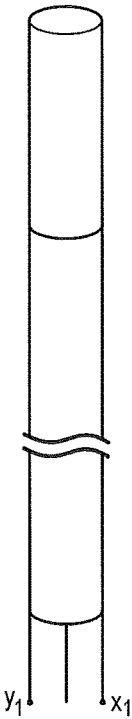
FIGS. 12A and 12B and 13A and 13B illustrate an exemplary benefit of the present disclosure in the articulation of a steerable catheter.
Figure 12B:
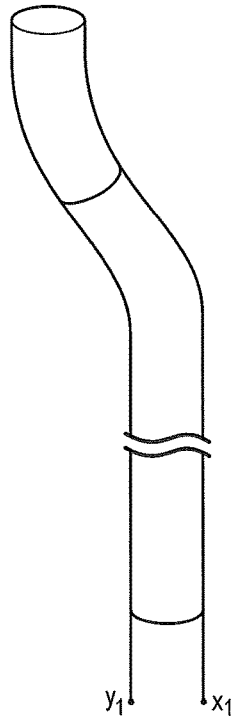

Indeed, using tension as a predictor of catheter angulations has numerous advantages beyond those discussed above. For example, when the shape of the catheter shaft is unknown as a result of anatomical constraints when inserted into vasculature, un-modeled shaft dynamics may result in unintended articulation. FIG. 12A shows a catheter with a straight shaft and control wires in positions $x_1$ and $y_1$; FIG. 12B shows the same catheter with the shaft bent—with the tip of the catheter bending to the right when the shaft bends to the right. Even though the pull-wires wires are held in their original positions for both conditions, namely $x_1$ and $y_1$, the tip of the catheter is bent to a new position. Because the shaft is no longer straight, the distal tip of the catheter is forced to bend in order to keep the total length between the proximal points $x_1$ and $y_1$ and the distal points $x_2$ and $y_2$ identical.

Figure 13A:
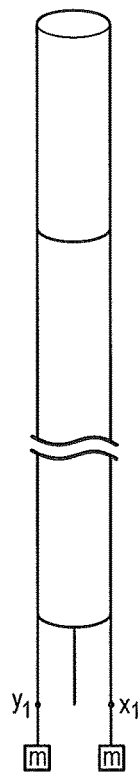
Figure 13B:
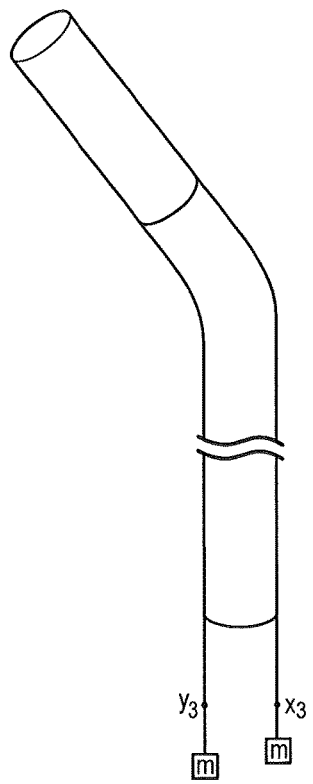

The use of a desired motor torque as the output instead of a desired motor position improves this issue. Turning to FIGS. 13A and 13B, the initial conditions are shown to be the same but the pull-wires are held under a constant tension. Viewing the kinematic model as weights hung from each wire, FIG. 13B illustrates the shaft bent in a similar manner as FIG. 12B, but the distal section remains straight as the path lengths of the pull wires need not be made identical as the constant tension in the control wires kept the distal section articulated to the same angle. The position of the pull-wire has changed to $x_3$ and $y_3$ to accommodate the bend in the shaft.

The present disclosure can also enable distal disturbance detection, i.e., when the distal tip of the catheter has been subjected to an unknown force in an unknown direction, often from tissue contact. Without the distal disturbance, a repeatable relationship exists between catheter pull-wire tension and position, but the disturbance changes the displacement and/or orientation of the tip. Because a difference between commanded and actual positions of the catheter will exist as a result of the disturbance, the length of the path of the control wires will be different than expected. These changes cause a difference in the tension of the wires, provided they are moved away from the commanded location. For instance, if the catheter is commanded to articulate to 180° but a distal disturbance prevents the catheter from bending past 90°, then the tension in the inner wires will be higher than expected and the tension in the outer fibers will be lower due to the difference in path lengths.

Figures 14, 15:
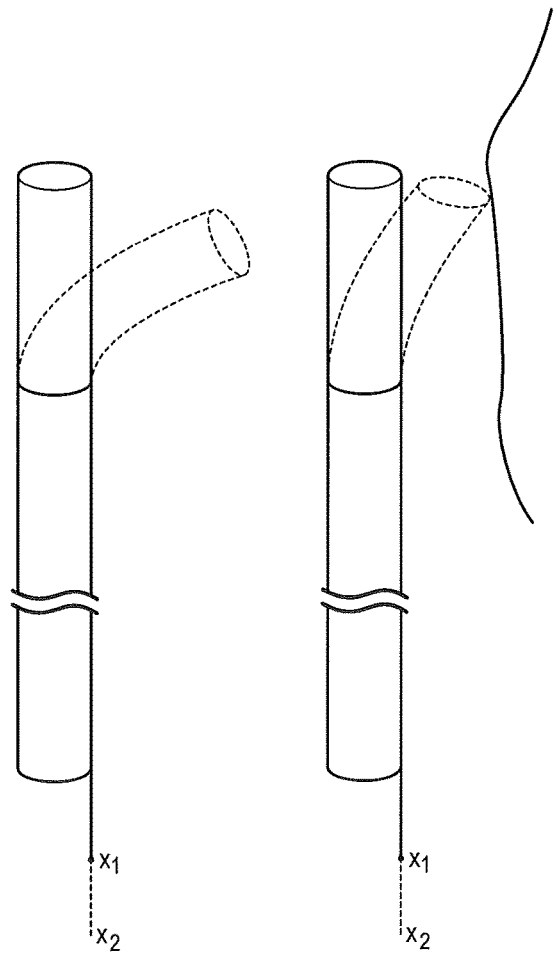
FIGS. 14 and 15 illustrate an exemplary benefit of the present disclosure in the articulation of a steerable catheter.

FIGS. 14 and 15 illustrate a distal disturbance. The amount of pull-wire motion can be correlated to motion expected at the distal section by using a spring model. Using motor torque to steer a catheter, the change in spring rate caused by a disturbance at the distal end of the catheter can be observed. When a disturbance at distal end prevents the catheter tip from achieving the commanded angulation, that resistance of motion at the distal section will effectively change the spring rate of the catheter shaft and the equations will fail to predict the motion. In this example, the angulation is commanded by moving the control wire from position $x_1$ to $x_2$. As governed by the equation, this change in spring rate can be determined via knowledge of the tension in the control wires. Thus, tension or motor torque data can be used to determine adjustments to the motor commands to achieve the desired tension and adjusting motor commands based on real time tension data. This information can also be fed back into the controls software and can be presented to the user as haptic, visual or other feedback to relay the effect of the disturbance.

The distal disturbance shown in FIG. 15 is caused by the catheter coming in contact with an external surface. An alternative distal disturbance may occur when a therapeutic device such as a stent, an atherectomy device or a balloon is being advanced through the catheter. The stiffness of this device cannot be previously modeled because the doctor can choose from a large variety and size range of devices. But a system with tension control can be used to ensure the angle of the tip of the catheter does not change. The increased spring rate of the catheter as the therapeutic device is being advanced can be detected by the tension sensors. Then, this tension or motor torque data can be used to determine adjustments to the motor commands to maintain the catheter tip position. This information can also be fed back into the controls software and can be presented to the user as haptic, visual or other feedback to relay the effect of the increased stiffness.

Embodiments of the present disclosure also have the advantage of enabling compensation for time dependent variables in like plastic creep, which changes the operational working length of the catheter but not the wires, causing tension to reduce over time. Creep compensation can also be compensated for if the tension in the control wires is known. Catheters are generally made from plastic laminates; plastics are known to change dimensions when subjected to external forces over time. This change over time is known as creep. However, with the present disclosure, if the tension in all the wires is less than expected, a catheter shaft length can be compensated for by returning the tensions to their expected values.

Figure 16:
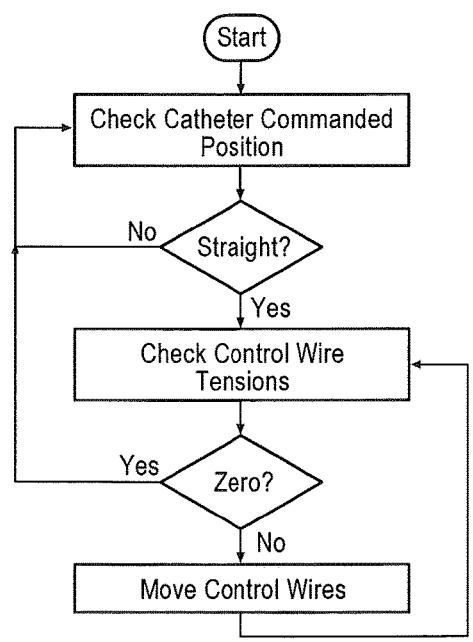
FIG. 16 is a flow diagram illustrating the use of tension information to equalize or eliminate tension in pull-wires.

Further, good control of a catheter can be obtained only if the motion expected to be transmitted to the controls wires are indeed transmitted. For a variety of reasons, motion intended to be transmitted to the articulating section may fail. Friction in the gearing or other mechanical aspects of the instrument driver may be problematic. Backlash in the drive transmission can be seen as slack or non-taut pull-wires. The control of the catheter can be improved if the scenario is detected and compensated for adequately, as shown in the flow chart of FIG. 16, through general re-zeroing of the pull-wire tension. The process of FIG. 16 may also be used to accommodate shaft shape compensation when the shaft has been subjected to new unknown forces. The tension on the control wires will be equal and near or equal to zero when the catheter articulating section is straight. However, if the shaft of the catheter has been deflected, and the catheter has been commanded to be straight, the tension in the catheter control wires will be non-equal. Thus, the equalization and reduction of tension to or near zero is contemplated by the present disclosure. Using tension sensing to take up wire slack may also be performed when the path length for an inside wire is shorter after a bend in the catheter, such as when the catheter is going contralateral over the iliac bifurcation. Further, another use of tension sensing to take up wire slack may occur for a catheter that has spiraled. Steerable catheters often spiral when pushed through the anatomy, resulting in a shorter path for one wire.

A pull-wire tension control paradigm can also inherently implement a safety check to ensure safe and reliable behavior. Exemplary variations of the present disclosure may include enabling tension limits on the control wires to prevent breakage, preventing articulation of the catheter when tension sensing indicates a distal disturbance from potential tissue contact (as discussed further above) and/or limiting the combined loading on the catheter shaft to prevent buckling. Specifically, the direct measurement of torque can signal if the tension in the pull-wire is approaching maximum limits. The catheter controls wires are made of steel and inherently have a breaking strength. One failure mode of catheters is when the pull wires break. This can be prevented by monitoring the tension in the cables and preventing them from being overstressed.

Further, the tension sensors can be monitored by comparing the motor current at any given moment with the tension measurements. Since the current is related to the torque applied by the motors, a discontinuity between the sensor readings and the current could indicate a potentially faulty tension sensor. Similarly, the present disclosure assists in shaft buckling prevention. The tensile loads in the catheter control wires are reacted by a compressive load in the catheter shaft. Like the wires in tension, the shaft has a loading limit in compression. This limit can be avoided by summing the tension in all the control wires and checking to see that they do not exceed the compressive strength of the shaft.

Another exemplary aspect of the present disclosure is that non-idealities such as signal saturation may be addressed. For example, an anti-windup algorithm may be included on the integral control term such that the commanded electrical torque, $\tau_{elec}$, will never actually exceed what the electronics are capable of producing. Similarly, all control terms are pre-saturated before adding them together to calculate $\tau_{elec}$ such that any one term cannot over-power the others when acting at the maximum of the available range.

Further, if a fault condition was detected when driving in tension control mode relating to the tension sensor or another aspect of the tension control mode, the system could be shut down the system or, in the alternative, an automatic switch to position control could be implemented. The tension control mode has the advantage of compatibility with the position control mode, enabling the two modes to back up the other. The catheter kinematics and solid mechanics for the modes enable smooth transition from tension control mode into position control mode. This would allow us to keep the doctor in control of the catheter in the case of a fault that only affects the tension sensing system without abruptly ending the procedure. Naturally, some care would have to be taken to avoid the potential for unintentional motion as the algorithms transition.

Another embodiment of the present disclosure would include the ability of a surgeon or other user to switch between the torque-based paradigm and the position-based paradigm, with one or the other serving as a default mode. For example, the position-based paradigm could be utilized as the default mode with the ability for a surgeon to switch to the torque-based mode for certain procedures. The control computer could automatically switch between the modes based on parameters that are input into the system or feedback during the procedure. Alternatively, the instrument driver may incorporate the desired motor torque value in a closed loop system. A variation of the present disclosure contemplates using both the position-based and torque-based paradigms during a surgical procedure, where, e.g., the system implements catheter articulation in the first instance through motor displacement commands but the associated desired motor torque is used to ensure that the desired deflection angle is achieved and/or maintained. Further, in another embodiment of the present disclosure, other modes of operation could be enabled, such as the ability of a constant force mode, in which the articulation force is maintained, creating a force against the tissue that is more uniform while crossing trabeculated tissue.

Another aspect of the current disclosure is to use the torque sensing capability on the pull-wires to pull all wires at the same time and stiffen the catheter. For typical articulation of a catheter as shown in FIG. 12A, one wire is pulled by a distance $x_1$ and the opposing wire is typically released by a distance y1. This delta wire displacement causes the tip of the catheter to deflect as described above. However, if both wires are pulled equal amounts, then the tip will not deflect. Instead, the tensioned wires inside the wall of the catheter serve to stiffen the catheter. One of catheter design challenge is that there are times when a catheter needs to be stiff to provide stability for delivering therapeutic devices through it and there are times when it needs to be flexible to navigate through tortuous vessels. Many conventional catheters attempt to overcome this issue by designing catheters with variable stiffness—that is to say the distal end is manufactured with less stiff materials than the proximal end. Tension sensing on the catheter pull wires allows dynamic variable stiffness. In other words, the catheter can be manufactured with less stiff materials and the doctor has the ability to increase tension on all wires and stiffen the catheter when required. It should be understood that this dynamic variable stiffness can be applied in any catheter configuration and with any given catheter tip articulation. For example, if one pull-wire is pulled by 1N more than another, then the catheter tip may be deflected 30°. The dynamic variable stiffness algorithm would now apply an additional 2N to each of the 2 wires to increase the stiffness. The delta between the two wires is still 1N so the tip does not change angle.

Operator workstation 112 may include a computer or a computer readable storage medium implementing the operation of instrument driver 108. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A system comprising:
   an elongated flexible medical instrument comprising an elongate member coupled to a distal portion of the medical instrument;
   an instrument driver coupled to a proximal end of the elongate member, the instrument driver comprising:
   a rotatable body configured to transmit torque from a motor, and
   a force sensor configured to generate an actual force signal based on an actual force; and
   a control system in communication with the instrument driver, the control system configured to:
   generate a command force signal in response to a user command from a user input device,
   provide the command force signal to the instrument driver to control movement of the distal portion of the medical instrument into a first position,
   receive the actual force signal from the instrument driver, and
   maintain the first position of the distal portion of the medical instrument via adjusting the command force signal provided to the instrument driver based on the actual force signal received from the instrument driver.

2. The system of claim 1, wherein the force sensor is further configured to provide a direct measurement of the actual force on the elongate member.

3. The system of claim 1, wherein the force sensor is further configured to measure a resistivity of the elongate member as a strain gauge.

4. The system of claim 1, wherein the force sensor comprises a torque sensor.

5. The system of claim 1, wherein the control system is further configured to detect a fault in the force sensor by comparing an expected force on the motor based on a current conveyed to the motor to an actual force detected by the force sensor.

6. The system of claim 1, wherein the rotatable body comprises a drive shaft.

7. The system of claim 1, wherein the motor is part of a motor servo.

8. The system of claim 1, wherein the rotatable body protrudes from a face of the instrument driver.

9. The system of claim 1, wherein a torque sensor is installed on the rotatable body.

10. The system of claim 1, wherein the rotatable body is coupled to a proximal end of the elongate member.

11. The system of claim 10, wherein the elongate member is configured to transmit a tension to the distal portion of the medical instrument to cause the medical instrument to articulate in response to a rotation of the rotatable body.

12. The system of claim 1, wherein the control system is configured to monitor a stress on the elongate member based on the actual force signal.

13. The system of claim 1, wherein the medical instrument comprises at least one of a catheter and an endoscope.

* * * * *